United States Patent [19]
Strickland

[11] Patent Number: 5,233,979
[45] Date of Patent: Aug. 10, 1993

[54] METHODS AND APPARATUS FOR A MICRO-TRACHEAL CATHETER HUB ASSEMBLY

[75] Inventor: Richard D. Strickland, Sandy, Utah

[73] Assignee: Ballard Medical Products, Draper, Utah

[21] Appl. No.: 780,263

[22] Filed: Oct. 21, 1991

Related U.S. Application Data

[63] Continuation-in-part of Ser. No. 602,426, Oct. 22, 1990.

[51] Int. Cl.⁵ .................. A61J 3/00; A61M 16/00
[52] U.S. Cl. .................. 128/207.14; 128/207.17; 604/283; 604/284; 604/905
[58] Field of Search .................. 128/207.14–207.17; 604/83–86, 283, 284, 905

[56] References Cited

U.S. PATENT DOCUMENTS

| | | |
|---|---|---|
| 2,127,215 | 8/1938 | Gwathmey . |
| 2,624,341 | 1/1953 | Wallace . |
| 2,912,982 | 11/1959 | Barsky . |
| 3,039,469 | 6/1962 | Fountain . |
| 3,599,642 | 8/1971 | Tindel . |
| 3,884,242 | 5/1975 | Bazell et al. . |
| 3,991,762 | 11/1976 | Radford . |
| 4,022,219 | 5/1977 | Basta . |
| 4,036,210 | 7/1977 | Campbell et al. . |
| 4,240,417 | 12/1980 | Holever . |
| 4,315,505 | 2/1982 | Crandall et al. . |
| 4,351,328 | 9/1982 | Bodai . |
| 4,557,261 | 12/1985 | Rügheimer . |
| 4,569,344 | 2/1986 | Palmer .................. 128/207.16 |
| 4,574,798 | 3/1986 | Heitzman . |
| 4,595,005 | 6/1986 | Jinotti . |
| 4,669,463 | 6/1987 | McConnell .................. 128/207.14 |
| 4,674,495 | 6/1987 | Orr .................. 128/207.14 |
| 4,674,496 | 6/1987 | Svadjian et al. .................. 128/207.16 |
| 4,681,100 | 7/1987 | Brychta et al. . |
| 4,723,543 | 2/1988 | Beran .................. 128/207.14 |
| 4,739,756 | 4/1988 | Horn .................. 128/207.14 |
| 4,815,459 | 3/1989 | Beran .................. 128/207.14 |
| 4,827,921 | 5/1989 | Rügheimer . |
| 4,838,255 | 6/1989 | Lambert . |
| 5,054,482 | 10/1991 | Bales .................. 128/207.14 |
| 5,083,561 | 1/1992 | Russo .................. 128/207.16 |

FOREIGN PATENT DOCUMENTS 8902761 4/1989 World Int. Prop. O. ...... 128/207.16

Primary Examiner—Stephen C. Pellegrino
Assistant Examiner—Glenn Dawson
Attorney, Agent, or Firm—Workman Nydegger Jensen

[57] ABSTRACT

The present invention relates generally to apparatus and methods used in trans-tracheal oxygen therapy to permit a micro-tracheal catheter to be inserted into the throat, so that breathing efficiency may be enhanced through the introduction of a continuous stream of oxygen directly into the patient's lungs. More particularly, this invention relates to an adapter for use on the outer end of the micro-tracheal catheter to connect the micro-tracheal catheter to an oxygen source through an oxygen supply hub while simultaneously and selectively permitting the introduction of a saline solution or other material into the patient's lungs through a second material supply hub. During the introduction of solution into the lungs, no oxygen is lost, and the stream of oxygen remains continuous.

14 Claims, 8 Drawing Sheets

METHODS AND APPARATUS FOR A MICRO-TRACHEAL CATHETER HUB ASSEMBLY

THE RELATED APPLICATIONS

This application is a continuation-in-part of copending application Ser. No. 07/602,426 filed Oct. 22, 1990 in the name of Richard D. Strickland and entitled "Methods and Apparatus for a Micro-Tracheal Catheter Hub Assembly," which is incorporated herein by specific reference.

BACKGROUND

2. Field of the Invention

The present invention relates generally to apparatus and methods for use in transtracheal oxygen therapy. More particularly, the present invention provides for a novel connector hub assembly which allows oxygen to be supplied through a micro-tracheal catheter while simultaneously introducing another material with the oxygen into the lungs of a patient.

3. The Background of the Invention

Patients suffering from chronic oxygen-dependent respiratory failure must have an almost constant supply of oxygen. Today, many patients with chronic oxygen-dependent respiratory failure use nasal cannulas as part of their oxygen therapy. With nasal cannula therapy, patients receive needed oxygen through tubes which extend from the oxygen supply into the nasal passages and are attached with a harness at the ears and nasal septum.

There are some disadvantages associated with nasal cannula therapy. One disadvantage is that before the oxygen can reach the lungs, it must first pass through the nasal passages, the back of the mouth, and the vocal chords. When administered through this route, much oxygen escapes from the mouth and the nose and is wasted. Three problems result from this loss of oxygen. One is that the oxygen saturation level of the patient is lower than it would otherwise be if the oxygen had not been wasted. This makes it more difficult for the patient to exercise, and exercise is often an important component of recovery for such patients. A second problem is that since much of the oxygen is wasted, patients are forced to carry with them larger containers of oxygen than would otherwise be necessary. For many, this is not only burdensome, but immobilizing, particularly in the case of persons who may be seriously physically weakened due to age or illness. A third problem is the financial burden placed upon patients to purchase oxygen supplies that are depleted by inefficient delivery.

An additional problem with the use of typical nasal cannula devices is discomfort. A constant flow of dry, cold oxygen in the nasal passages causes drying of delicate nasal membranes. This drying can cause the nasal passage tissues to swell and become irritated. As a consequence, less oxygen is delivered through the swollen nasal passages making breathing more difficult so that frequently, a patient will attempt to breathe through the mouth, which further complicates the drying problem. This problem is especially acute during the night when oxygen saturation levels are already at their lowest.

In addition, because the nasal cannula is attached around the ears of the user, the harness often irritates the tops of the ears. Because of these side-effects of nasal cannula therapy, patients have been reluctant to continuously wear such nasal cannula devices as prescribed. Thus, the effectiveness of the therapy is reduced.

In addition to the inefficient use of oxygen with nasal cannula, the need to draw oxygen through the nasopharyngeal and larygotracheal dead space contributes to dyspnea and leads to recruitment of the accessory muscles of respiration. The use of these muscles requires exertion which in turn increases the need for oxygen.

Devices and methods have been developed which solve many of these problems. One such method, called transtracheal oxygen delivery, uses a micro-tracheal catheter inserted into the trachea through the skin at the base of the throat. On the end of the catheter is attached a luer connector which couples the catheter through an oxygen supply tube to an oxygen source. With the use of this device, oxygen is neither lost nor wasted because it is delivered into the trachea directly above the lungs. Thus, oxygen delivery is more efficient. This efficiency allows patients to be more mobile because they may carry around smaller containers of oxygen. Another advantage is better oxygen saturation as a result of delivery closer to the lungs.

To overcome many of the disadvantages of other methods, micro-tracheal catheters were developed to have as little impact on a patient's lifestyle as possible. The catheter was developed to be as small as possible and still be capable of delivering the necessary one to six (1-6) liters per minute flow required by most adult patients. The supply tube from the oxygen supply may be concealed under the patient's clothing and the supply itself is often contained in an easy-to-carry and discrete container. Even the puncture and installation procedure itself takes little more than fifteen minutes and recovery is usually swift.

After local and topical anesthesia is administered, a puncture is made and the micro-tracheal catheter is inserted into the trachea between two of its upper cartilaginous rings. Insertion is usually accomplished with an internal needle or needle, guidewire, dilator technique.

The microtracheal catheter is slid over the guidewire into the bronchial tree. The guidewire reduces trauma and the risk of kinking.

At this point, the catheter is completely advanced into the trachea until the retention strap abuts the skin and the catheter is no longer visible. With the guidewire serving as a roentgenologic marker, chest radiographs can be performed to document the positioning of the catheter. The guidewire is then removed and the retention strap is sutured to the neck and secured around the patient's neck to retain the catheter in place. Oxygen is later attached and the previous method of oxygen delivery removed.

The benefits of the micro-tracheal catheter often include the restoration of smell and taste and occasionally libido. The appliance has little cosmetic intrusion and mobility is higher than with any other form of treatment. As a result of these benefits, patients often resume pretreatment activities and generally achieve a higher standard of life.

This device and method also solve the problem of irritation of the nose and face. Since the oxygen does not have to pass through the nose, the nasal tissues do not become dry and irritated. Further, there are no facial attachments to irritate or encumber the face and ears.

A further advantage of the micro-tracheal catheter and method is the fact that it assists the patient in breathing. Breathing requires a certain amount of work. If a patient has chronic obstructive lung disease, the amount of work needed to breathe is increased. This work is reduced by the delivery of oxygen directly to the lungs under the pressure of an oxygen tank. Thus, with transtracheal oxygen delivery a patient is able to work less to get the same volume of oxygen to the lungs.

The size of the micro-tracheal catheter requires a much smaller opening (0.2 to 0.3 cm long) than that required for transtracheal tubes formerly used and is, therefore, more cosmetically appealing than either nasal cannula or larger tracheal tubes.

As illustrated in FIG. 1, when a transtracheal catheter is placed in the trachea, it must be able to make an abrupt bend after the catheter passes through the neck of the patient so as to extend the distal end of the catheter down toward the lungs. This bend serves to assist in locating the micro-tracheal catheter at the back of the trachea and away from the more sensitive sides. Since transtracheal catheters are directly connected to the oxygen supply tube through the luer connector, or to the neck through sutures, no rotation of the oxygen supply tube in relation to the neck is allowed. If the catheter is not flexible enough and does not have sufficient circular memory and resiliency, certain kinds of abrupt action such as swallowing, turning the head, coughing and the like will tend to result in kinking, and possibly irritation to the sides of the trachea.

Another problem associated with transtracheal catheters arises from the direct introduction of oxygen into the trachea. Such introduction bypasses the natural moisturizing action of the upper respiratory tract. Oxygen dries the trachea and lungs and so, requires regular irrigation with saline solution. Irrigation loosens secretions, stimulates expectoration, and moisturizes the lungs.

With existing systems, irrigation is accomplished by disconnecting the patient from oxygen and instilling saline solution into the transtracheal catheter of the patient. Droplets of the saline solution then contact the carina, and that cough center is stimulated to violent coughing. While this coughing action helps to clear the bronchial pathways, loosens secretions and cleanses the respiratory tract, coughing involves the expenditure of work and therefore, is an oxygen consumptive activity. The period when a patient requires the most oxygen is exactly at the time that the oxygen is disconnected. This situation often results in hypoxia during instillation. Since instillation is required from two to four times daily, it is easy to see why patient compliance has historically been low.

Another problem associated with the droplet nature of the solution being introduced is its inability to penetrate into the lungs for any distance. The droplets remain consolidated and are carried back up in the violent coughing that accompanies their presence near the carina.

A new problem associated with the small size of the micro-tracheal catheter occurs during irrigation. As the oxygen pressure is disconnected and saline solution introduced, the mucous dislodged by the violent coughing often fouls the tip of the micro-tracheal catheter plugging the opening thereof. This plugging may require the extraction of the catheter for cleaning or an additional irrigation procedure. Extraction necessitates the discontinuation of oxygen delivery. Other means must be used, such as nasal cannula or masks, if the patient must endure without oxygen for a period while the catheter is cleaned. In some early micro-tracheal catheters this operation was required several times a day. While more modern catheters are constructed of materials to resist mucous build-up and clogging, violent coughing continues to occasionally plug the micro-tracheal catheter tip when no oxygen flow is present.

Another problem arising from the small size of the microtracheal catheter is illustrated in FIG. 1. The relatively heavy oxygen supply line, because of its connection to the micro-tracheal catheter some distance from the throat, tends to move the catheter about the trachea. This movement causes irritation or tickling of the trachea and may eventually wear on the sensitive sides of the trachea as the catheter is jostled from its usual position resting on the rear of the trachea. This movement causes coughing and discomfort and may eventually create irritation to the sides of the trachea.

Many physicians take advantage of the ability of the micro-tracheal catheter to inject medication directly into the lungs. This process will also require the discontinuation of oxygen to the patient with the same resultant lapse in oxygen delivery. The medication is injected into the micro-tracheal catheter with a syringe or other device and enters the lungs in droplet form. While this introduction method is preferred over oral introduction, penetration into the lungs is still limited by the droplet form of the medication.

Further disadvantage of the transtracheal catheters in use today are the fact that the material is introduced directly against the neck of the patient. This causes irritation to the already tender stoma.

Additionally, inserting the material directly against the neck cannot be done with ease, as the user cannot see what he or she is doing without using a mirror, and the hands are placed in an awkward position.

BRIEF SUMMARY AND OBJECTS OF THE INVENTION

It is, therefore, an object of the present invention to provide apparatus and methods for the simultaneous introduction of oxygen and a material, such as a saline solution, into the lungs of a patient through a micro-tracheal catheter, avoiding in the process the hypoxic effects of disconnecting the oxygen supply of the patient.

It is another object of the present invention to provide apparatus and methods for the aerosolization of materials before introduction into the lungs to avoid the negative into the lungs.

It is a further object of the present invention to provide apparatus and methods capable of resisting blockage of the tip of a micro-tracheal catheter from mucous accumulating on the catheter or being coughed-up from the lungs.

A yet further object of the present invention is to provide apparatus and methods that resist forces applied to the oxygen supply tube from being transferred to the micro-tracheal catheter thereby causing irritation and discomfort.

It is yet another object of the present invention to provide apparatus and methods allowing a micro-tracheal catheter to rotate within the means used to retain it to the micro-tracheal opening.

A still further object of the present invention is to provide apparatus and methods allowing the simultaneous constant flow of oxygen and the instillation of a medication into the lungs of a patient.

An additional object of the present invention is to provide apparatus and methods allowing ease of handling during insertion of the material into the catheter, and allowing insertion to be done with reduced irritation to the stoma.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention is directed to an apparatus and methods of use involving a connector hub assembly for use on the outer end of a micro-tracheal catheter to connect the micro-tracheal catheter to a continuous supply of oxygen through an oxygen supply hub while simultaneously and selectively permitting the introduction of a saline or other medicamentous solution or material into the patient's lungs through a material supply hub.

To facilitate intermixing before introduction into the lungs, a mixing chamber is provided. This mixing chamber communicates at one end with a supply port which is in direct communication with the micro-tracheal catheter, and at the other end with two hubs, an oxygen supply hub and a material supply hub. The oxygen supply hub provides means for attaching an oxygen supply tube for communication with a continuous supply of oxygen. The second material supply hub provides means for attaching a material supply tube for selective introduction of materials to be intermixed with the continuous supply of oxygen in the mixing chamber and transported therewith to the lungs.

A housing encloses the mixing chamber, and is attached to both the oxygen supply and material supply hubs and to the supply port which connects the proximal end of the microtracheal catheter In a presently preferred embodiment of the invention, the axis of the oxygen supply hub is aligned with the axis of the mixing chamber to provide direct access to the mixing chamber and micro-tracheal catheter. The material supply hub axis is oriented at an angle to the mixing chamber and oxygen supply hub to form a Y connection. Upon connection to an oxygen supply tube and oxygen supply, the oxygen supply hub provides a constant flow of oxygen to the patient. If the introduction of a material, such as a saline solution or other medication or material is desired, the material supply tube is opened by removing therefrom a tethered cap, and a device, such as a syringe, is used to introduce the material into the constant stream of oxygen flowing through the mixing chamber. A material supply adaptor allows the supply of material to be coupled to the material supply tube.

The constant flow of oxygen through the mixing chamber and the micro-tracheal catheter ensures that the tip of the catheter remains clear as mucous is coughed up from the lungs. In the presently preferred embodiment within the scope of the invention, the oxygen stream is constant without fear of leakage through the opening of the material supply tube. Located within the material supply adaptor is a one-way check valve which allows entry of material into the material supply tube but prevents exit of oxygen. The one-way check valve prevents escape of oxygen even when there is no supply of material attached to the material supply tube.

The presently preferred embodiment of the present invention provides for rotation of the supply port of the connector hub assembly within a restraining device used for maintaining contact between supply port of the connector hub assembly and the micro-tracheal opening in the trachea of the patient. This rotational ability allows the connector hub assembly to be used with the oxygen supply on either side of the patient and redirects forces applied by movement of the neck into the more rigid oxygen supply tube instead of being transferred into the micro-tracheal catheter. This arrangement not only allows the patient to choose the oxygen supply placement, but also lessens the possibility of chaffing inside the trachea from movements of the neck.

The supply port of the connector hub assembly is located in direct contact with the throat of the patient. This placement allows the neck to absorb pivoting forces applied to the supply port of the connector hub assembly by any motion of the oxygen supply tube, which in turn lessens movement of the micro-tracheal catheter inside of the trachea. Reduced chaffing of the interior of the trachea results.

In keeping with the desire to limit the movement of the micro-tracheal catheter inside the trachea of the patient, the presently preferred embodiment also provides straps for limiting the movement of the oxygen supply tube.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode for making and using the invention will be described and explained with additional specificity and detail through the use of the accompanying drawings in which.

DETAILED DESCRIPTION OF THE PREFERRED EMBODIMENT

Figure 1:
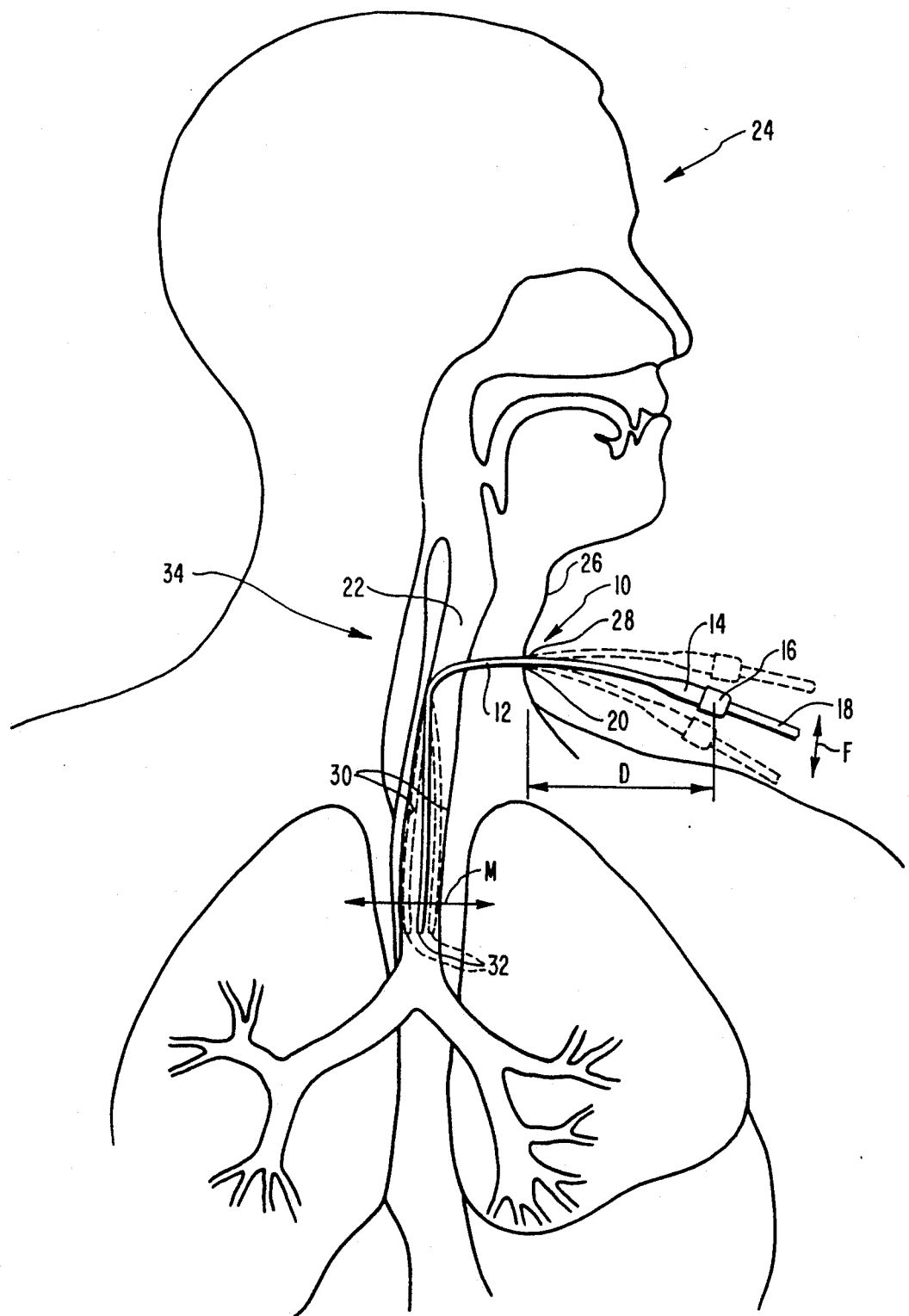
FIG. 1 is a schematic view showing a patient with a prior art device inserted through a micro-tracheal opening.

FIG. 1 illustrates a prior art device 10 comprised of a micro-tracheal catheter 12 joined at a proximal end 14 to an oxygen supply joint 16 and an oxygen supply tube 18. Prior art device 10 is inserted through a puncture wound 20 into a trachea 22 of a patient 24. FIG. 1 illustrates in dashed lines the movement caused to micro-tracheal catheter 12 by the prior art. In prior art device 10, oxygen supply tube 18 is connected to micro-tracheal catheter 12 at a distance D from a throat 26. Distance D allows oxygen supply tube 18 to act as a lever arm translating forces F along micro-tracheal catheter 12 to a puncture site 28. Puncture site 28 acts as a pivot point to translate movement caused by forces F to be translated into pivoting forces applied to micro-tracheal catheter 12. FIG. 1 illustrates in dashed lines the pivoting action of micro-tracheal catheter 12. The movement of micro-tracheal catheter 12 causes chaffing against a trachea side 30 causing irritation. The movement of a distal end 32 of micro-tracheal catheter 12 is directly proportional to the movement of oxygen supply tube 18. Movements in oxygen supply tube 18 are transferred to puncture site 28 where torsion may be developed as a result of the direct connection between oxygen supply tube 18 and micro-tracheal catheter 12. No allowance is made to relieve puncture site 28 of the torsional forces applied on it. Movements caused by motion in a neck 34 are also directly transferred into micro-tracheal catheter 12 at puncture site 28.

Figure 2:
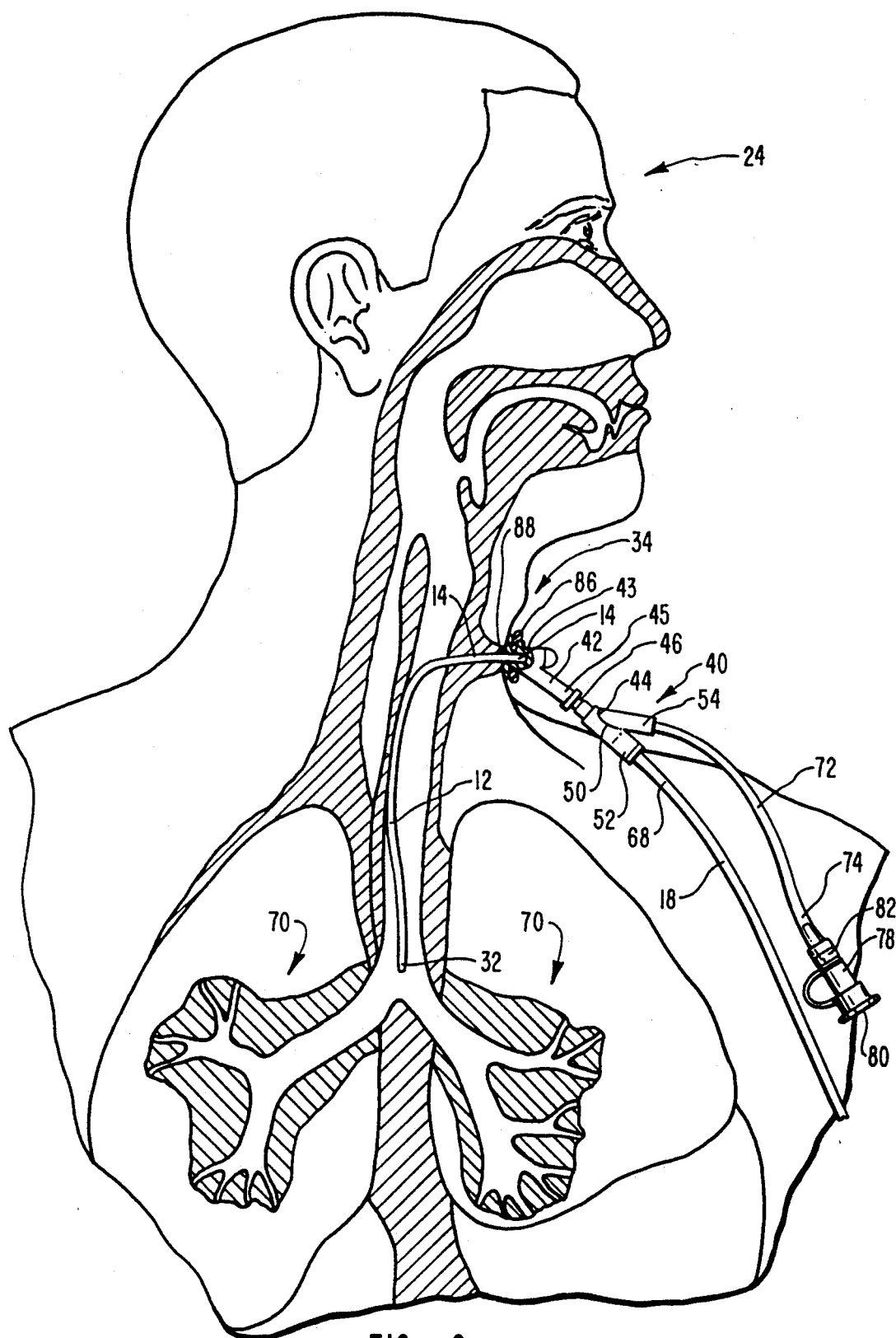
FIG. 2 is a schematic view of one presently preferred embodiment of the present invention attached to a micro-trachael catheter placed in the trachea of a patient.

In FIG. 2, a connector hub assembly 40 incorporating teachings of the present invention is illustrated. Connector hub assembly 40 comprises a supply port 42 through which oxygen and other material are passed before entering into the multi-tracheal catheter 12. Supply port 42 is coupled at a first end 43 to the proximal end 14 of micro-tracheal catheter 12 and couplable at a second end 45 to a general supply juncture 44. One possible means for coupling supply port 42 to general supply juncture 44 in the preferred embodiment of the present invention is a male luer slip fitting 46, which is attached to general supply juncture 44 and which inserts into the second end 45 of supply port 42, thereby coupling and allowing communication between general supply juncture 44 and supply port 42.

General supply juncture 44 is formed of a mixing chamber 50 in direct communication with supply port 42, an oxygen supply hub 52 communicating at one end thereof with mixing chamber 50 and couplable at the other end thereof with a supply of oxygen 56, and a material supply hub 54 communicating at one end thereof with mixing chamber 50 and couplable at the other end thereof with a supply of material. Material supply hub 54 is oriented at an angle from the longitudinal axis of mixing chamber 50. Oxygen supply hub 52 is aligned with and parallel to the longitudinal axis of mixing chamber 50 allowing a direct path for the introduction of oxygen into the supply port 42.

Oxygen is passed from the supply of oxygen 56 to the oxygen supply hub 52 through an oxygen supply tube 18. Oxygen supply tube 18 contains a source end 66 which is connectable to supply of oxygen supply 56, and a delivery end 68 which is connectable to the oxygen supply hub 52. Oxygen passes from the supply of oxygen 56 through the oxygen supply tube 18 to the oxygen supply hub 52. Oxygen is then passed through the supply port 42 into the multi-tracheal catheter 12 where it exits distal end 32 of catheter 12 into the lungs. Oxygen may be supplied to the lungs 70 in a continuous stream.

Other materials, such as a saline solution for example, may also be introduced into the lungs simultaneously with the oxygen. The material may be passed from the supply of material to material supply hub 54 through a material supply tube 72. Material supply tube 72 is couplable at a material source end 74 to the supply of material 58 and coupled at an opposite material delivery end 76 to the material supply hub 54.

As both material supply hub 54 and oxygen supply hub 52 are in communication with mixing chamber 50, oxygen passing through oxygen supply hub 52 and material passing through material supply hub 54 meet within mixing chamber 50. In mixing chamber 50, the material intermixes with the stream of oxygen and is transported therewith through supply port 42 and into micro-tracheal catheter 12.

The supply of material is made capable of coupling with material supply tube 72 by a material supply adaptor 78. Material supply adaptor 78 is attached to the material source end 74 and provides a means for attaching supply of material 58 to material supply tube 72. If, for example, supply of material is a syringe, the material supply adaptor 78 allows temporary attachment of the syringe to the material supply tube 72 such that material can flow from the syringe to the material supply tube 72. In the preferred embodiment within the scope of the present invention, the material supply adaptor is made of a flexible material which allows various sizes of syringes as well as other suppliers of materials, such as any size of unit dose vials, to be accommodated. In the preferred embodiment, the flexible material is vinyl.

Also connected to material supply adaptor 78 is a tethered cap 80 which is fitted to close off material supply adaptor 78 when there is no supply of material 58 attached. Although in the preferred embodiment tethered cap 80 is tethered to material supply adaptor 78, it will be appreciated that other locations for tethering the cap is also possible and within the scope of the present invention.

Within the material supply adaptor 78 is an important feature of the present invention which prevents oxygen from leaking out of material supply tube 72 when there is no supply of material attached. This important feature is a one-way check valve 82 located at the material source end 74 within the material supply adaptor 78. This one-way check valve 82 allows material to enter material supply tube 72 while simultaneously preventing oxygen from exiting. Additionally, oxygen is prevented from exiting the material supply tube 72 by the one-way check valve 82 even when neither tethered cap 80 nor a supply of material is attached.

It is important to note that with the present invention, the connector hub assembly 40 is positioned in close proximity with the throat. Referring to FIG. 2, distance D as seen in FIG. 1 is not present in the present invention as illustrated in FIG. 2. The supply port 42 of connector hub assembly 40 abuts throat 26 and so reduces the lever arm of oxygen supply tube 18. This in turn reduces movement against the puncture site 28 on the neck which would otherwise have been transferred to the micro-tracheal catheter 12 and which would have caused chafing and irritation to the trachea.

Figure 3:
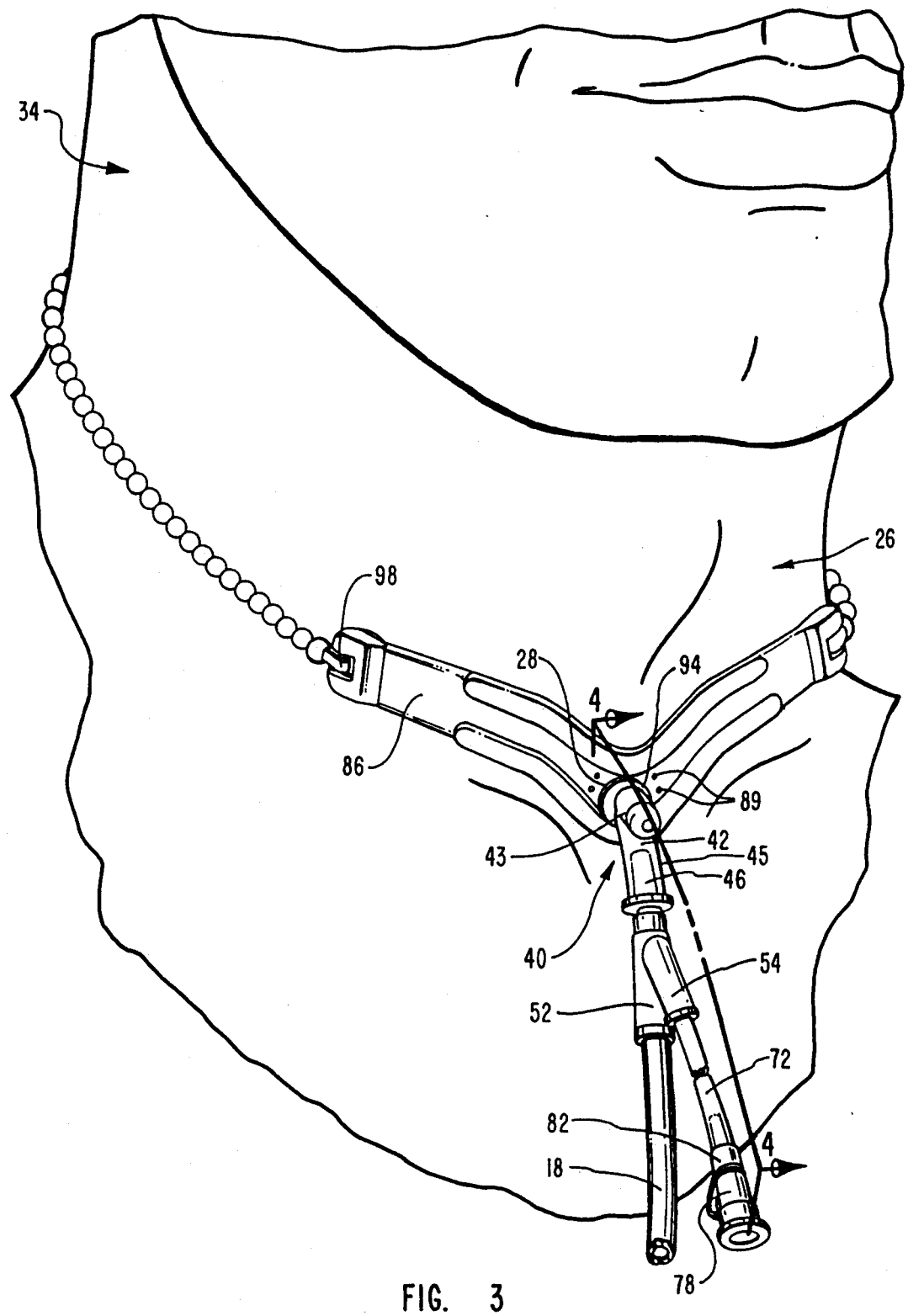
FIG. 3 is an enlarged prospective view of a preferred embodiment of the present invention illustrating the placement of the present invention at the throat of a patient.

The advantage of having supply port 42 positioned so closely to the neck 34 of the user is made possible in the present invention by retention means for retaining the supply port 42 in place. As can be seen in FIG. 3, the retention means in the preferred embodiment within the scope of the present invention comprises a strap 86 of flexible material joined to the first end of supply port 42 and configured so as to be able to encircle neck 34 and hold supply port 42 in position adjacent neck 34. Strap 86 is attached to the first end of supply port 42 by an attaching button 88 having a hole 90 therein for passage of micro-tracheal catheter 12. Strap 86 is securely sandwiched between attaching button 88 and supply port 42 of connector hub assembly 40 such that when strap 86 is placed around neck 34, the secured supply port 42 is stabilized against the neck. Suture holes 89, formed near the joint of strap 86 with the first end of supply port 42, hold strap 86 to neck 34.

Attaching button 88 also serves as rotation means for allowing torsional forces caused by movement of the oxygen tube 18 to be translated into rotational movement of the supply port 42, at a rotational area 94, about the longitudinal axis of micro-tracheal catheter 12 rather than allowing the forces to be transferred to strap 86 and the puncture site 28 to which strap 80 is sutured. Again, this rotational capability prevents the excess chafing and irritation to the trachea from torsional movement around the neck 34.

Figure 6:
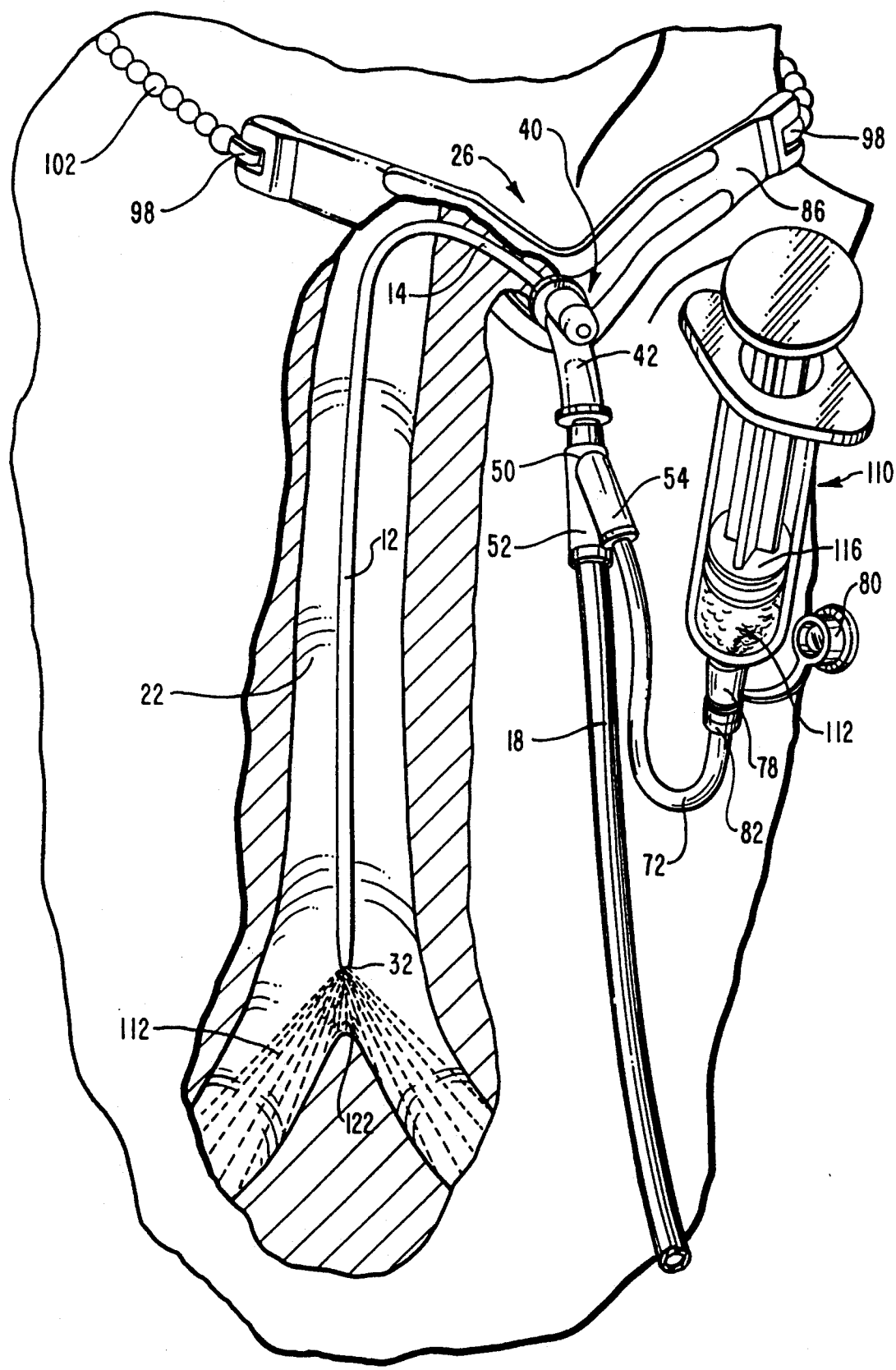
FIG. 6 is sectional view illustrating the introduction of a material through the material supply hub of a presently preferred embodiment of the present invention.
Figure 7:
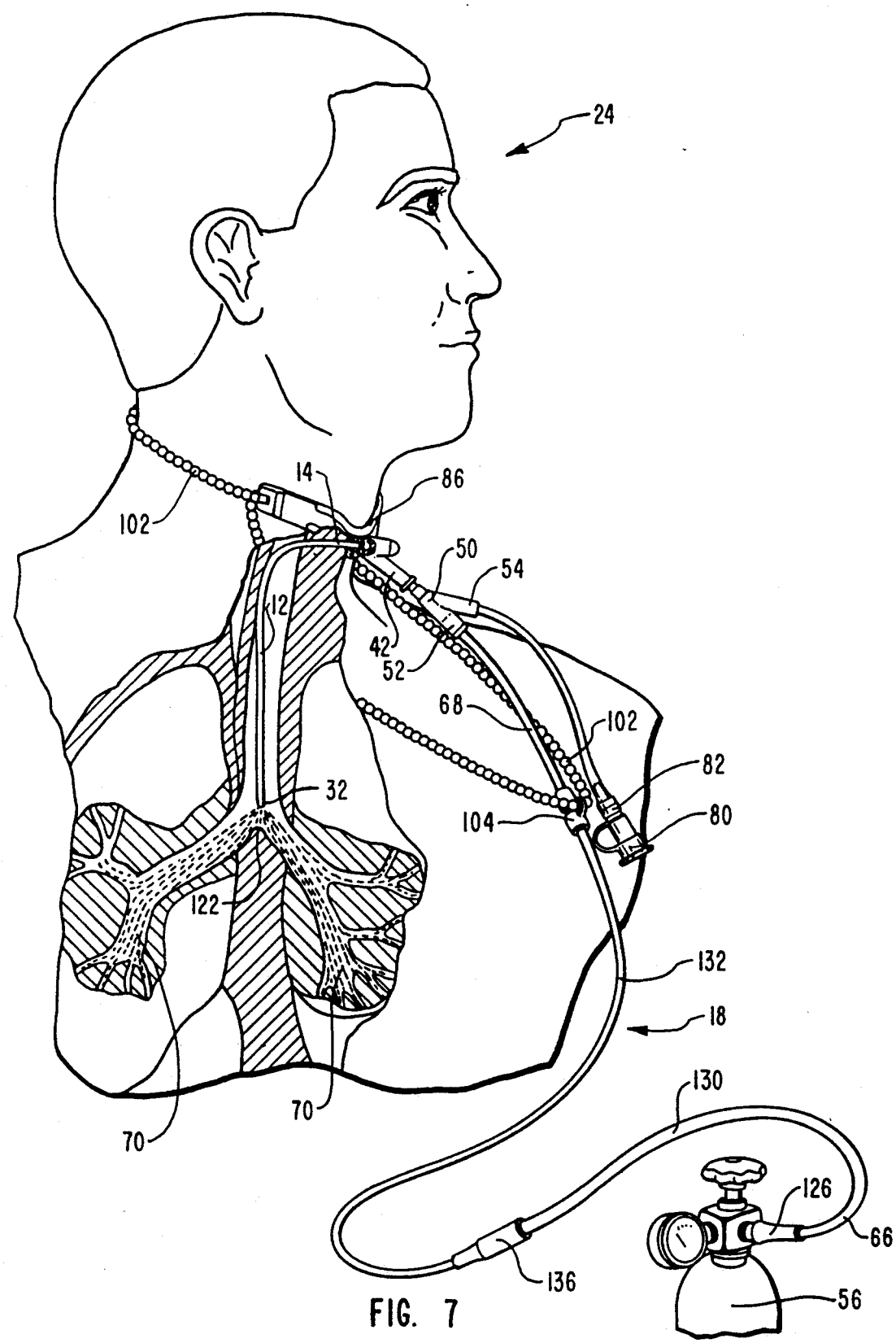
FIG. 7 is a perspective view with portions broken away particularly illustrating placement of the transtracheal catheter in a patient's trachea, and which illustrates the elements of a system for simultaneously introducing oxygen and a material through a micro-tracheal catheter.

The retention means for retaining supply port 42 to throat 26 of patient 24 may further be seen in FIGS. 3, 6, and 7. In the illustrated embodiment of the present invention, strap 86 is provided with attachment holes 98 for connection to a support strap or chain 102 which further secures strap 86 around the neck 34. In the preferred embodiment within the scope of the present invention, support chain 102 extends around neck 34 through attachment holes 98 and connects with oxygen tube 18 at a friction cuff 104, such that the weight of oxygen tube 18 is not completely held by the supply port 42, but is also supported by the support chain 102 extending around the neck of the user. Support chain 102 serves to reduce the transference of stress from the oxygen supply tube 18 to the supply port 42.

While the retention means as described above is preferred, it can be appreciated that other retention means may also be employed within the scope of the present invention to retain supply port 42 and the entire connector hub assembly 40 securely to the neck of the patient. For example, instead of one support chain 102, there may be two separate chains extending around the neck, one for securing the strap 86 around the neck, and one for supporting the weight of the oxygen tube.

Figure 4:
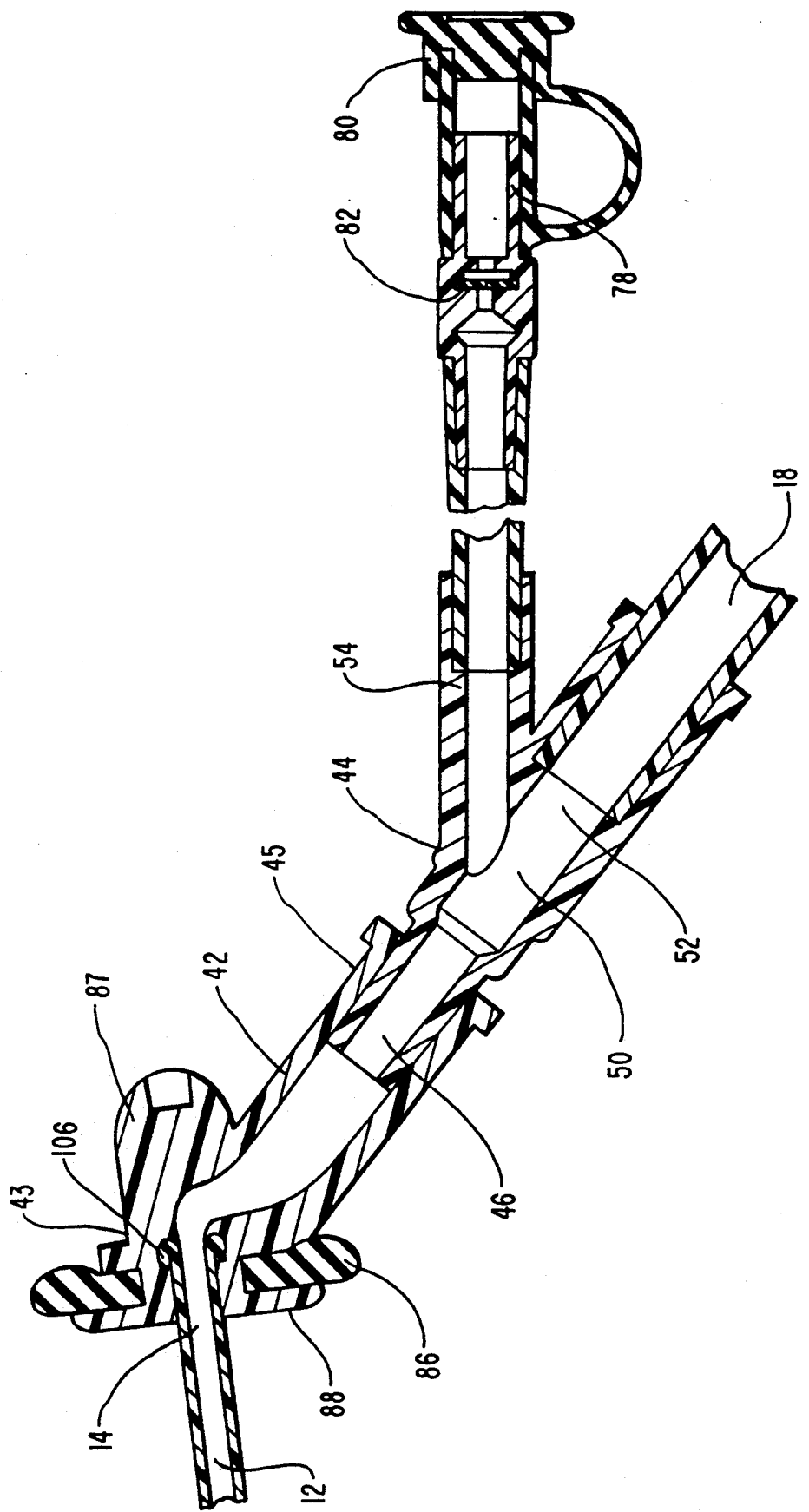
FIG. 4 is a cross-sectional view taken along line 4—4 of FIG. 3, illustrating the connection of the oxygen supply hub and the material supply hub to the supply port and the interrelationship of the micro-tracheal catheter, supply port, mixing chamber, oxygen supply hub and the material supply hub.

Turning now to FIG. 4, the connection between micro-trachael catheter 12 and supply port 42 in relation with the rotation means and the retention means can be seen. As mentioned above, micro-tracheal catheter passes through hole 90 of attachment button 88. The proximal end 14 of catheter 12 is mechanically locked into place against attachment button 88 by being flared into a tab 106, the tab 106 preventing multi-tracheal catheter 12 from passing back through hole 90 once the proximal end 14 is inserted. Thus, it can be seen that in the preferred embodiment within the scope of the present invention, both supply port 42 and multi-tracheal catheter 12 are held to strap 86 by attachment button 88.

In the preferred embodiment within the scope of the present invention, the catheter is also held attached to attachment button 88 which is a part of submember 87 by insert molding processes well known in the art. No gluing operation is necessary.

Further illustrated in FIG. 4 is the passageway system within the connector hub assembly 40. It can be seen that general supply juncture 44 has within it passageways communicating between oxygen supply hub 52, material supply hub 54, and mixing chamber 50. The passageway of mixing chamber 50 in turn communicates freely with supply port 42, which as stated earlier, is connectable to the mixing chamber end of the general supply juncture 44 by male luer slip fitting 46, and which, in turn, forms a passageway which communicates freely with micro-tracheal catheter 12. Oxygen and other materials may move freely through these passageways. A Y orientation of material supply hub 54, oxygen supply hub 52, and supply port 42 which allows free and adjoining passageways can be seen.

Figure 5:
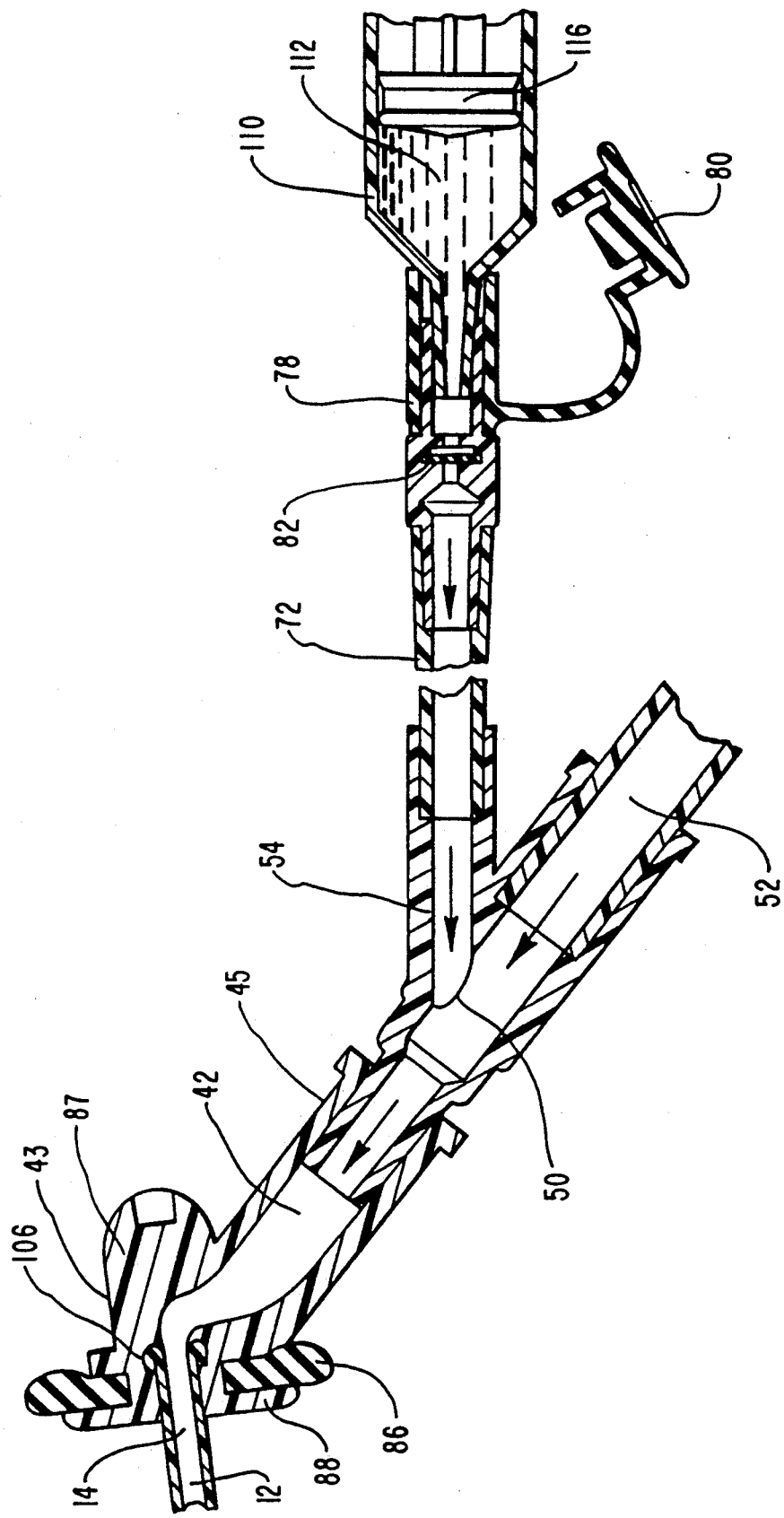
FIG. 5 is a cross-sectional view taken along line 4—4 of FIG. 3, illustrating the material supply hub and related structures.

FIG. 5 illustrates the introduction of material through the material supply tube 72, and into the material supply hub 54. In FIG. 5, the supply of material comprises a syringe 110. Initially, syringe 110 is made couplable to material supply tube 72 by the material supply adaptor 78. As can be seen in FIG. 4, a tethered cap 80 attached to the material supply adaptor 78 is used to cover the opening of material supply adaptor 78 when it is not in use. In FIG. 5, tethered cap 80 has been removed in preparation for attachment of syringe 110 to material supply tube 72.

Figure 8:
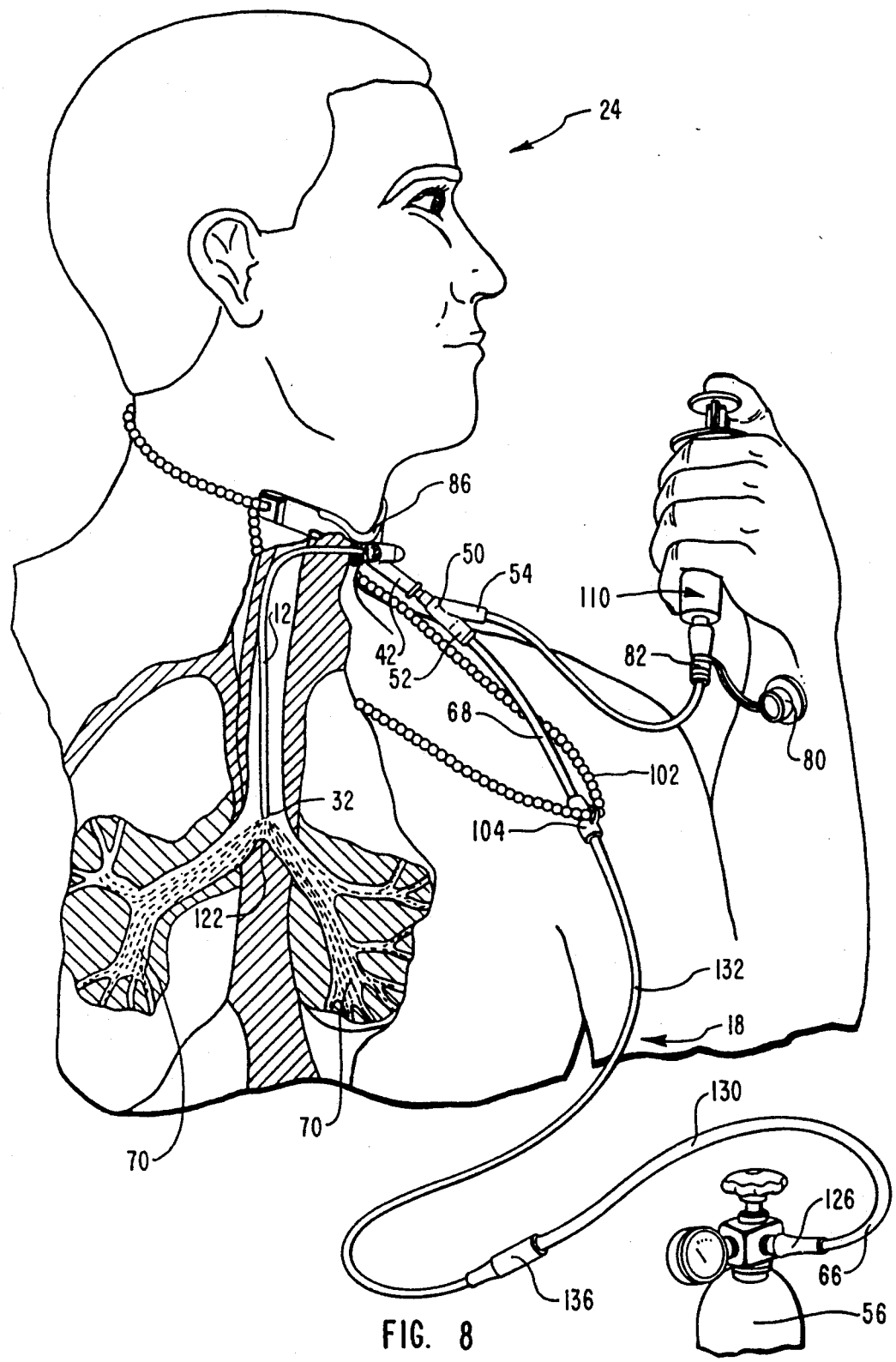
FIG. 8 is a perspective view with portions broken away, particularly illustrating use of the hub assembly such that introduction of material into the material supply tube can be clearly viewed by the user.

After attachment of syringe 110 through material supply adaptor 78, a material 112 is introduced into material supply tube 72. A plunger 116 compresses material 112 out of an injector 118 and into material supply tube 72. This material 112 proceeds through the material supply tube 72 to the material supply hub 54 where it then passes to the mixing chamber 50. There, material 112 is intermixed with and becomes aerosolized by the continuous flow of oxygen coming through the oxygen supply hub 52. (This continuous flow of oxygen is illustrated with arrows as is the flow of material from syringe 110.) After intermixing, material 112 is forced out of mixing chamber 50 and into the supply port 42, where it is then transported to the proximal end 14 of micro-trachael catheter 12 by the continuous flow of oxygen. The mixture then proceeds down the catheter and exits into lungs 70.

FIG. 6 further illustrates the introduction of material 112 into the lungs. As can be seen, material supply tube 72 connects the supply of material to the material supply hub 54. A material supply adaptor 78 on the end of material supply tube 18 is where the supply of material 58 is inserted. The material supply tube 18 allows supply of material 58 to not be inserted directly into the material supply hub 54. This allows material 112 to be introduced at a spot away from the neck, with an advantage being that when syringe 110, or other supply of material is inserted, pressure is not placed directly on the neck. One hand may hold the material supply adapter 78 which accepts the syringe 110, while the other hand may insert the syringe. In contrast, in a system where the syringe is inserted directly against the neck, excess pressure is placed upon the already tender stoma.

An additional advantage of being able to insert the supply of material, such as the syringe 110, away from the neck is that the user can easily see what he or she is doing, without having to use a mirror, or without having to guess at the correct positioning of the insertion. Introduction of the material away from the neck is more fully illustrated in FIG. 8. The user is able to hold the syringe 110 in his or her hand and freely observe as he or she inserts the syringe 184 into the material supply adaptor 154. Therefore, handling of the connector hub assembly 40 is uncomplicated and manageable.

Further, when insertion of the supply of material 58 is performed away from the neck, the user is able to insert the syringe 110, or other supply of material such as a unit dose vial or metered dose inhalant, and hold it in a vertical, upright position during introduction of the material into the body. In this position, gravity assists in allowing all of the solution to be introduced into the body. In contrast, in former systems where insertion was directly against the neck, the supply of material had to be positioned horizontally during introduction of material. Thus, when unit dose vials were used as the supply of material, releasing all of the material from the horizontally positioned unit dose vials into the body was difficult.

Returning now to the introduction of material illustrated in FIG. 6, it can be seen that plunger 116 forces material 112 out of syringe 110, through material supply hub 54 and into mixing chamber 50. Material 112 is intermixed with the constant stream of oxygen that is flowing from oxygen supply tube 18, through oxygen supply hub 52 and also into mixing chamber 50. Upon intermixing, material 112 is forced by the continuous passage of oxygen through supply port 42 and into micro-tracheal catheter 12. Material 112 then flows through micro-tracheal catheter 12 until material 112 exits through distal end 32. Material 112 and the oxygen that is intermixed with material 112 will enter trachea 22 in an aerosolized form and be drawn deep into the lungs of patient 24. The aerosolized form of material 112 allows the material to remain suspended in the breath of patient 24 longer than large droplets. In addition, aerosolized material 112 will not irritate a person's carina 122, the sensitive tip of the branching portion of the lungs, thereby avoiding the violent coughing associated with irritation of the carina cough center.

Tethered cap 80 is shown attached to material supply adaptor 78 but removed from the opening. Strap 86 holds connector hub assembly 40 snugly against throat 26 to allow throat 26 to absorb much of the pivotal force applied by connector hub assembly 40. The broad resilient strap 86 is joined to a smaller portion of the retention means by a smaller support strap 102.

FIG. 7 illustrates a system for simultaneously introducing oxygen and material 112 through micro-tracheal catheter 12. A supply of oxygen 56 is connected to oxygen supply tube 18 by an oxygen supply connector 126 at a source end 66. Oxygen supply tube 18 is divided into a first portion with a larger bore 130 for durability and a second portion with a smaller bore 132 for ease of concealment under clothing. Oxygen flowing from supply of oxygen 56 flows first through larger bore 130 to a reducing step-down unit 136 where the larger bore is 130 is reduced to that of smaller bore 132. The oxygen flow leaves smaller bore 132 at a delivery end 68 where it enters oxygen supply hub 52 and passes through micro-tracheal catheter 12 and into the lungs 70 of patient 24. Support chain 102 attaches at one end to the body of patient 24 and at the other end to a friction cuff 104 slidably attached to oxygen supply tube 18 to reduce the communication of stresses placed on the oxygen supply tube from being transferred to transtracheal catheter 12.

Strap 86 maintains contact between supply port 42 and throat 26 of patient 24. Tethered cap 80 is tethered to material supply adaptor 78 and closes off entrance into material supply tube 72 when a supply of material 58 is not in use.

From the foregoing, it will be appreciated that a substantial advantage of the connector hub assembly of the present invention is that because of the communicating configurations of the oxygen supply hub and the material supply hub, oxygen and a material such as saline solution can be introduced into the lungs simultaneously, without any interruption in the flow of oxygen. Additionally, with the present invention, irritation to the trachea is reduced by a configuration and retention means which allow resistance against forces applied to the oxygen supply tube from being transferred to the micro-tracheal catheter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A connector hub assembly connected to an ambulatory user's throat, said connector hub assembly adapted for coupling a micro-trachael catheter to a supply of oxygen and to a supply of a material to be mixed with oxygen so as to be supplied through the catheter without interrupting the supply of oxygen, said connector hub assembly comprising:

(a) a supply port having a first and second end, the first end being adapted for direct communication with the micro-trachael catheter;

(b) a general supply juncture removably attachable to the second end of the supply port and comprising:

(1) a mixing chamber communicating with the supply port;

(2) an oxygen supply hub having two ends, one end communicating with the mixing chamber and the other end adapted to be coupled to the supply of oxygen;

(3) a material supply hub having two ends, one end communicating with the mixing chamber and the other end connected to one end of a length of a material supply tube so as to be couplable to the supply of material at a distal end of the material supply tube, the length of the material supply tube being long enough to permit the user to grasp the distal end and hold it in a manner such that the distal end can be seen by the user when connecting the distal end to the supply of material, and the material when introduced into the material supply hub becoming mixed in the mixing chamber with the oxygen and transported therewith through the micro-tracheal catheter an into the lungs of the user; and (4) means for removably attaching the general supply juncture to the second end of the supply port.

2. A connector hub assembly as defined in claim 1, wherein the means for removably attaching the general supply juncture to the supply port is a male luer slip fitting couplable with the supply port.

3. A connector hub assembly as defined in claim 1, wherein said material supply hub comprises:
 (a) a material supply adaptor attached to the distal end of the material supply tube for coupling the distal end to the supply of material;
 (b) a cap fitted to close the material supply adapted when the material supply tube is not coupled to the supply of material, thereby closing the material supply tube; and
 (c) a one-way check valve located within the material supply adaptor, the one-way check valve being configured such that it eliminates accidental interruption of oxygen flow by allowing solution to go into the material supply tube from the supply of material while simultaneously preventing oxygen from going out of the material supply tube, and the one-way check valve being configured to prevent escape of oxygen even when the material supply tube is not closed by the cap.

4. A connector hub assembly as defined in claim 3, wherein said cap is tethered to the material supply adaptor.

5. A connector hub assembly as defined in claim 1, wherein said general supply juncture forms passageways having a Y-shaped structure providing communication between the mixing chamber, the supply port, the oxygen supply hub, and the material supply hub.

6. A connector hub assembly as defined in claim 5, wherein:
 (a) said material supply hub comprises a material supply leg of said Y shaped structure;
 (b) said oxygen supply hub comprises an oxygen supply leg of said Y shaped structure; and
 (c) said mixing chamber comprises a mixing chamber leg of said Y shaped structure said mixing chamber leg removably couplable to the supply port.

7. A connector hub assembly, connected to an ambulatory user's throat, said connector hub assembly adapted for coupling a micro-tracheal catheter to a supply of oxygen and to a supply of a material to be mixed with oxygen so as to be supplied through the catheter without interrupting the supply of oxygen, said connector hub assembly comprising:
 (a) a supply port having a first end and a second end, the first ending being adapted for direct communication with the micro tracheal catheter;
 (b) a general supply juncture removably attachable to the second end of the supply port, the general supply juncture comprising:
  (1) a mixing chamber;
  (2) an oxygen supply hub having two ends, one end communicating with the mixing chamber and the other end adapted to be coupled to the supply of oxygen;
  (3) a material supply hub having two ends, one end communicating with the mixing chamber and the other end adapted to be coupled to one end of a length of a material supply tube so as to be couplable to the supply of material at a distal end of the material supply tube, the length of the material supply tube being long enough to permit the user to grasp the distal end and hold it in a manner such that the distal end can be seen by the user when connecting the distal end to the supply of material, and the material when introduced into the material supply hub becoming mixed in the mixing chamber with the oxygen and transported therewith through the micro-tracheal catheter and into the lungs of the user; and
 (c) retention means for retaining the supply port of the connector hub assembly against the throat of the user while allowing the supply port to be rotated relative to said retention means about the longitudinal axis of said micro-tracheal catheter.

8. A connector hub assembly as defined in claim 7, wherein said retention means comprises a strap of flexible material joined to the first end of the supply port.

9. A connector hub assembly as defined in claim 8, wherein said strap further comprises suture holes formed near the joint with the first end of the supply port.

10. A connector hub assembly as defined in claim 9, wherein said strap further comprises means for securing the supply port to the throat of the user.

11. A connector hub assembly as defined in claim 9, wherein said strap further comprises rotation means for allowing torsional forces to move the connector hub assembly while retained to the throat.

12. A connector hub assembly as defined in claim 11, wherein said rotation means comprises:
 (a) an attaching button affixed to the first end of the supply port of the connector hub assembly; and
 (b) a hole formed in the strap allowing rotational movement of the strap about the attaching button.

13. A connector hub assembly as defined in claim 7, wherein said material supply hub comprises:
 (a) a material supply adaptor attached to the distal end of the material supply tube, for coupling the distal end to the supply of material;
 (b) a cap fitted to close the material supply adaptor when the material supply tube is not being coupled to the supply of material, thereby closing the material supply tube; and
 (c) a one-way check valve located within the material supply adaptor, the one-way check valve being configured such that it eliminates accidental interruption of oxygen flow by allowing solution to go into the material supply tube from the supply of material while simultaneously preventing oxygen from going out of the material supply tube, and the one-way check valve being configured to prevent escape of oxygen even when the material supply tube is not closed by the cap.

14. A connector hub assembly connected to an ambulator user's throat, said connector hub assembly adapted for coupling a micro-tracheal catheter to a supply of oxygen and to a supply of a material to be mixed with oxygen so as to be supplied through the catheter without interrupting the supply of oxygen, said connector hub assembly comprising:
 (a) a supply port having a first and second end, the first end being adapted for direct communication with the micro-tracheal catheter;
 (b) a general supply juncture removably attachable to the second end of the supply port and comprising:
  (1) a mixing chamber;
  (2) an oxygen supply hub having two ends, one end communicating with the mixing chamber and the other end adapted to be coupled to the supply of oxygen; and
  (3) a material supply hub having two ends, one end communicating with the mixing chamber and the other end connected to one end of a material supply tube, the material supply tube being couplable at a distal end to the supply of the material and having a sufficient length such that the distal end can be grasped and held up so that the distal end can be viewed by the user when connecting it to the supply of material, and the material when introduced into the material supply hub becoming mixed in the mixing chamber with the oxygen and transported therewith through the micro-tracheal catheter and into the lungs of the user;

(c) a material supply adaptor for coupling the material supply tube to the supply of material;

(d) a cap fitted to close the material supply adaptor when the material supply tube is not being coupled to the supply of material, thereby closing the material supply tube;

(e) a one-way check valve located within the material supply adaptor, the one-way check valve being configured such that it eliminates accidental interruption of oxygen flow by allowing solution to go into the material supply tube from the supply of material while simultaneously preventing oxygen from going out of the material supply tube, and the one-way check valve being configured to prevent escape of oxygen even when the material supply tube is not closed by the cap;

(f) a retention strap comprised of a pliable, resilient material in which suture holes are formed and comprising means for attachment to a support chain at ends of said retention strap; and (g) an attaching button affixed to the supply port of the connector hub assembly and attached to said retention strap so as to allow rotational movement of the connector hub assembly.

* * * * *

UNITED STATES PATENT AND TRADEMARK OFFICE
CERTIFICATE OF CORRECTION

PATENT NO. : 5,233,979
DATED : August 10, 1993

INVENTOR(S) : RICHARD D. STRICKLAND

It is certified that error appears in the above-indentified patent and that said Letters Patent is hereby corrected as shown below:

Column 1, line 14, "2." should be --1.--
Column 1, line 22, "3." should be --2.--
Column 2, line 5, "larygotracheal" should be --laryngotracheal--
Column 4, line 50, after "negative" insert --reaction of the carina to droplets and to increase penetration--
Column 6, line 62, after "is" insert --a--
Column 11, line 60, delete first occurrence of "is"
Column 12, line 61, "an" should be --and--

Signed and Sealed this

Twelfth Day of April, 1994

Attest:

BRUCE LEHMAN

Attesting Officer

*Commissioner of Patents and Trademarks*